United States Patent
Kamen et al.

(10) Patent No.: US 9,478,022 B2
(45) Date of Patent: Oct. 25, 2016

(54) METHOD AND SYSTEM FOR INTEGRATED RADIOLOGICAL AND PATHOLOGICAL INFORMATION FOR DIAGNOSIS, THERAPY SELECTION, AND MONITORING

(75) Inventors: Ali Kamen, Skillman, NJ (US); Leo Grady, Millbrae, CA (US); Gianluca Paladini, Skillman, NJ (US); Parmeshwar Khurd, San Jose, CA (US); Oliver Kutter, Princeton, NJ (US); Dorin Comaniciu, Princeton Junction, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 355 days.

(21) Appl. No.: 14/240,534

(22) PCT Filed: Aug. 22, 2012

(86) PCT No.: PCT/US2012/051869
§ 371 (c)(1),
(2), (4) Date: Jul. 10, 2014

(87) PCT Pub. No.: WO2013/028762
PCT Pub. Date: Feb. 28, 2013

(65) Prior Publication Data
US 2014/0314292 A1    Oct. 23, 2014

Related U.S. Application Data

(60) Provisional application No. 61/525,929, filed on Aug. 22, 2011.

(51) Int. Cl.
*G06K 9/00* (2006.01)
*G06T 7/00* (2006.01)
(Continued)

(52) U.S. Cl.
CPC ............. *G06T 7/0012* (2013.01); *A61B 6/463* (2013.01); *A61B 6/467* (2013.01); *A61B 8/463* (2013.01);
(Continued)

(58) Field of Classification Search
None
See application file for complete search history.

(56) References Cited

U.S. PATENT DOCUMENTS

| | | | |
|---|---|---|---|
| 2008/0187095 A1* | 8/2008 | Boone et al. ........ | A61B 6/0435 378/37 |
| 2008/0221929 A1* | 9/2008 | Brackett ............... | G06F 19/321 705/3 |
| 2009/0093715 A1* | 4/2009 | Downey et al. ..... | A61B 8/0833 600/437 |

FOREIGN PATENT DOCUMENTS

| WO | 2006089426 | 8/2006 |
|---|---|---|
| WO | 2006119426 | 11/2006 |

OTHER PUBLICATIONS

P. Khurd et al., "Network Cycle Features: Application to Computer-Aided Gleason Grading of Prostate Cancer Histopathological Images"; In: Int. Symp. Biomedical Imaging, IEEE, pp. 1632-1636, 2011.

(Continued)

*Primary Examiner* — Atiba O Fitzpatrick

(57) ABSTRACT

A method and system for integrating radiological and pathological information for cancer diagnosis, therapy selection, and monitoring is disclosed. A radiological image of a patient, such as a magnetic resonance (MR), computed tomography (CT), positron emission tomography (PET), or ultrasound image, is received. A location corresponding to each of one or more biopsy samples is determined in the at least one radiological image. An integrated display is used to display a histological image corresponding to the each biopsy samples, the radiological image, and the location corresponding to each biopsy samples in the radiological image. Pathological information and radiological information are integrated by combining features extracted from the histological images and the features extracted from the corresponding locations in the radiological image for cancer grading, prognosis prediction, and therapy selection.

28 Claims, 5 Drawing Sheets

(51) Int. Cl.
    A61B 6/00     (2006.01)
    A61B 8/00     (2006.01)
    G06F 19/00    (2011.01)
    A61B 6/12         (2006.01)
    A61B 8/08         (2006.01)
    A61B 10/02        (2006.01)
(52) U.S. Cl.
    CPC ............... A61B 8/465 (2013.01); A61B 8/467 (2013.01); G06F 19/345 (2013.01); G06F 19/3481 (2013.01); A61B 6/12 (2013.01); A61B 8/0841 (2013.01); A61B 10/02 (2013.01); G06T 2207/30004 (2013.01)

(56) References Cited

OTHER PUBLICATIONS

International Search Report.

* cited by examiner

METHOD AND SYSTEM FOR INTEGRATED RADIOLOGICAL AND PATHOLOGICAL INFORMATION FOR DIAGNOSIS, THERAPY SELECTION, AND MONITORING This application claims the benefit of U.S. Provisional Application No. 61/525,929, filed Aug. 22, 2011, the disclosure of which is herein incorporated by reference.

BACKGROUND OF THE INVENTION

The present invention relates to integrating radiological and pathological information, and more particularly to integrating information from radiological scans, such as but not limited to magnetic resonance (MR), computed tomography (CT), positron emitted tomography (PET), and ultrasound (US) scans, and pathological information derived from biopsy samples for diagnosis, therapy selection, and treatment or disease monitoring.

In conventional clinical workflows, physicians perform biopsies of suspicious lesions or masses. For example, a urologist may perform a transrectal random-core biopsy of the prostate gland in order to search for cancerous tissue samples in patients with high prostate-specific antigen (PSA) blood test results. Specimens from the biopsy are sent to a pathology laboratory, where a pathologist generates a diagnosis in a written report that goes back to the referring physician and an oncologists, who determines the results to be concordant or discordant with other clinical indicators, such as radiological imaging findings from a radiologist. The oncologist then recommends appropriate management based on all the findings.

In the exemplary conventional workflow above, there it can be difficult to effectively communicate, perform correlation, and gather consensus of findings' concordance. These difficulties are primarily due to physical separation, geographic constraints, time, resources, and labor. Also, there is no access to larger sets of data with the known outcome, from which a clinician can draw resemblances and similarities for better final diagnosis and clinical decisions.

Recently, there have been attempts to introduce an updated digital pathology consultation protocol, which is described as follows. The radiologist informs the pathologist of cases that need to be discussed in a conference via an email message. The pathologist selects representative slides for scanning by a digital pathology system that can capture images of entire slides. During the conference digital microscopic images are accessed remotely and simultaneously on desktops of as many individuals as needed using digital pathology information management software. Corresponding radiological studies are uploaded to the radiologist's desktop via a radiology picture-archiving communications system (PACS). The entire diagnostic team including radiologists, pathologists, and surgeons, as well as nurses, residents, and students communicate with each other via a video conferencing system, which, in combination with a Web camera and linked computers, allows video conference sharing of desktop items, including radiological images, while maintaining an opportunity to communicate with and see each other electronically.

While the recently proposed system facilitates much need communication, it falls short in many aspects. For example, it is nearly impossible to establish spatial correlation between biopsy samples and groups of pixels within radiological images, meaning that one cannot tell where the biopsies were taken relative to the anatomical information provided by the radiological images. This can be a cause of discordance, for example, for micro-calcifications in breast cancer cases. Another cause of discordance is inter and intra operator variability, which can cause the need for repeat biopsies. When discordance between the radiological imaging and the histology cannot be resolve, an expensive surgical procedure may be required.

BRIEF SUMMARY OF THE INVENTION

The present invention provides a method and system for integrating radiological (e.g., MR, CT, PET, and ultrasound) and pathological information for diagnosis, therapy selection, and disease monitoring. Embodiments of the present invention can be applied to clinical scenarios where biopsy is the primary pathological modality. Embodiments of the present invention provide a data integration process or integrating pathology and radiology information that takes into account spatial correspondences between biopsy locations and radiological image data. Embodiments of the present invention utilize image analytics and additional information (e.g., from advanced targeted biomarkers) to provide automated reading and evaluation of the pathological and radiological information.

In one embodiment of the present invention, at least one radiological image of a patient is received. A location corresponding to each of one or more biopsy samples is determined in the at least one radiological image. An integrated display is used to show one or more histological images corresponding to the one or more biopsy samples, the at least one radiological image, and the location corresponding to each of the one or more biopsy samples in the at least one radiological image.

In other embodiments of the present invention, pathological information and radiological information are integrated by combining features extracted from the histological images and the features extracted from the corresponding locations in the radiological image for cancer grading, prognosis prediction, and therapy selection.

These and other advantages of the invention will be apparent to those of ordinary skill in the art by reference to the following detailed description and the accompanying drawings.

DETAILED DESCRIPTION

The present invention is directed to a method and system for integrating radiological and pathological information. Embodiments of the present invention are described herein to give a visual understanding of radiological and pathological information integration method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, it is to be understood that embodiments of the present invention may be performed within a computer system using data stored within the computer system.

Accurate cancer diagnosis, therapy selection, and treatment and disease monitoring heavily depends on both information from radiological scans (e.g., magnetic resonance (MR), computed tomography (CT), positron emission tomography (PET) and ultrasound) and pathological information derived primarily from biopsy samples. This often requires consultation and interaction among various clinicians, such as radiologists, pathologists, oncologists, and surgeons. Embodiments of the present invention provide a system where all the information can be stored and accessed at different times by various clinicians, and potentially from multiple sites via a high speed network. The system can establish correlation between a histological diagnosis resulting from a biopsy and radiological images. Such correlation can lead to recognition of whether a tumor was properly or inadequately sampled. The information provided by the system can lead to better recognition of tumor characteristics, while minimizing additional testing, repeat biopsies, and surgical excision. Furthermore, knowledge about tumor locations and integration of biopsy findings can be used to accurately plan and guide targeted therapies.

Embodiments of the present invention provide an integrated system that can be utilized in clinical scenarios where a biopsy is the primary pathological modality. The integrated system performs a data integration process for integrating pathology and radiological information that determines the spatial correspondences between the biopsy locations and the radiological imaging data. The integrated system may also rely on image analytics and addition information (e.g., from advanced targeted biomarkers) to provide automated reading and evaluation processes.

Figure 1:
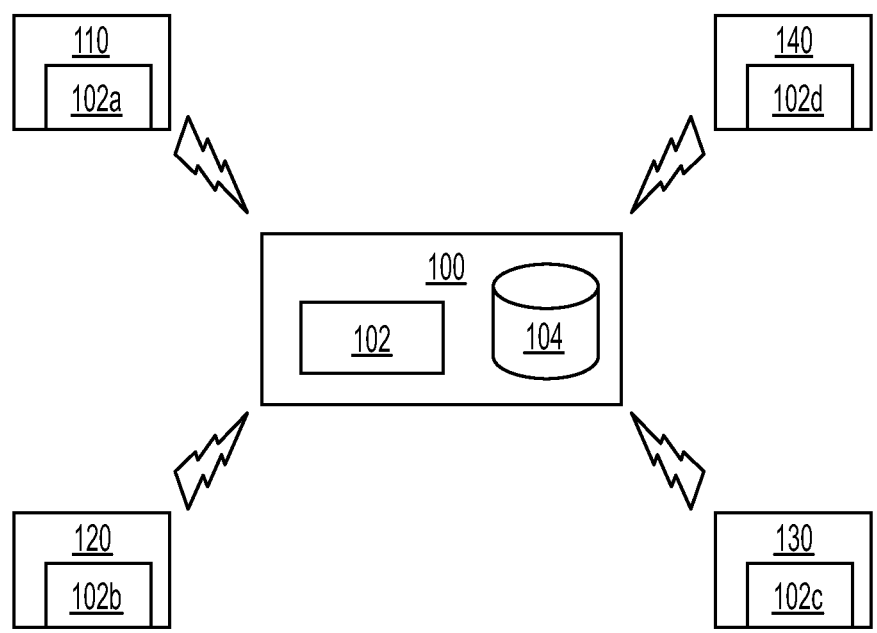
FIG. 1 illustrates a system for providing integrated radiological and pathological information for cancer diagnosis, therapy selection, and monitoring according to an embodiment of the present invention.

FIG. 1 illustrates a system for providing integrated radiological and pathological information for cancer diagnosis, therapy selection, and monitoring according to an embodiment of the present invention. As illustrated in FIG. 1, an integrated software platform 102 is run on one or more computing devices 100, 110, 120, 130, and 140 and integrates clinical data including radiological images and pathological slices. In the example of FIG. 1, a server 100 runs the integrated software platform 102 and also includes a database 104 to store the clinical data for various patients, as well as other data determined by or entered into the software platform 102. The integrated software platform 102 components are scalable to run on a broad spectrum of computing devices 110, 120, 130, and 140, from high-performance workstations to mobile computing platforms, with role-dependent, adaptable, multi-user graphic user interfaces 102a, 102b, 102c, and 102d that provide user control and data visualization for various users. The graphical user interface 102a-102d is adaptable based on the role and responsibilities of each respective clinical user (e.g., radiologist, surgeon, pathologist, oncologist) and settings for each graphical user interface 102a-102d can also be adapted to control the data accessibility and the available functionalities to manipulate and extract extra information from the data. The computing devices 110, 120, 130, and 140 can communicate with the server 100 and with each other via a high-speed network, such as the Internet, wirelessly or through a wired connection using secure communication protocols. In the embodiment of FIG. 1, the server 102 running the software platform 102 executes computer program instructions to perform various algorithms to process the radiological and pathological information, and the graphical user interfaces 102a-102d allow users at the computing devices to interact with the software platform 102 running on the server 102. In an alternate embodiment, different instances of the integrated software platform can be independently run on separate computing devices, such that the computer program instructions to perform the algorithms to process the radiological and pathological information can be performed locally at a given computing device, and the radiological information, pathological information, and any other patient data resulting from the algorithms can then be stored on a communal database.

The software platform 102 includes computer program instructions to perform various analytics that enable automatic grading and/or detection of important morphological or texture information from histological slides (i.e., pathological data) resulting from a biopsy. The most discriminant features across various levels of cancer versus non-cancer, malignant versus benign, or in the case of prostate cancer, Gleason grading are trained based on labeled training samplings using machine-learning techniques, such as support vector machines (SVM), probabilistic boosting trees (PBT), random forest, and trained regression functions. For example, Gleason grading for histological slices of the prostate can be automatically determined by the software platform 102 by a trained SVM using the method described in P. Khurd, et al., "Network cycle features: Application to Computer-Aided Gleason Grading of Prostate Cancer Histopathological Images," In *Biomedical Imaging: From Nano to Macro*, 2011 IEEE International Symposium on Biomedical Imaging, pages 1632-1636, the disclosure of which is incorporated herein by reference. The analytics capabilities are integrated within the software platform 102 and can be invoked on demand using the graphical user interface 102a-102d. Furthermore, according to an advantageous embodiment of the present invention, analytics can be performed together on both the radiological and pathological (histological) images in order to better establish co-occurrence of diagnostically valuable patterns. For pathological images, cancer specific staining procedures, for example using fluorophore tracers, provide additional information where analytics can be applied to extract differentiating features.

Figure 2:
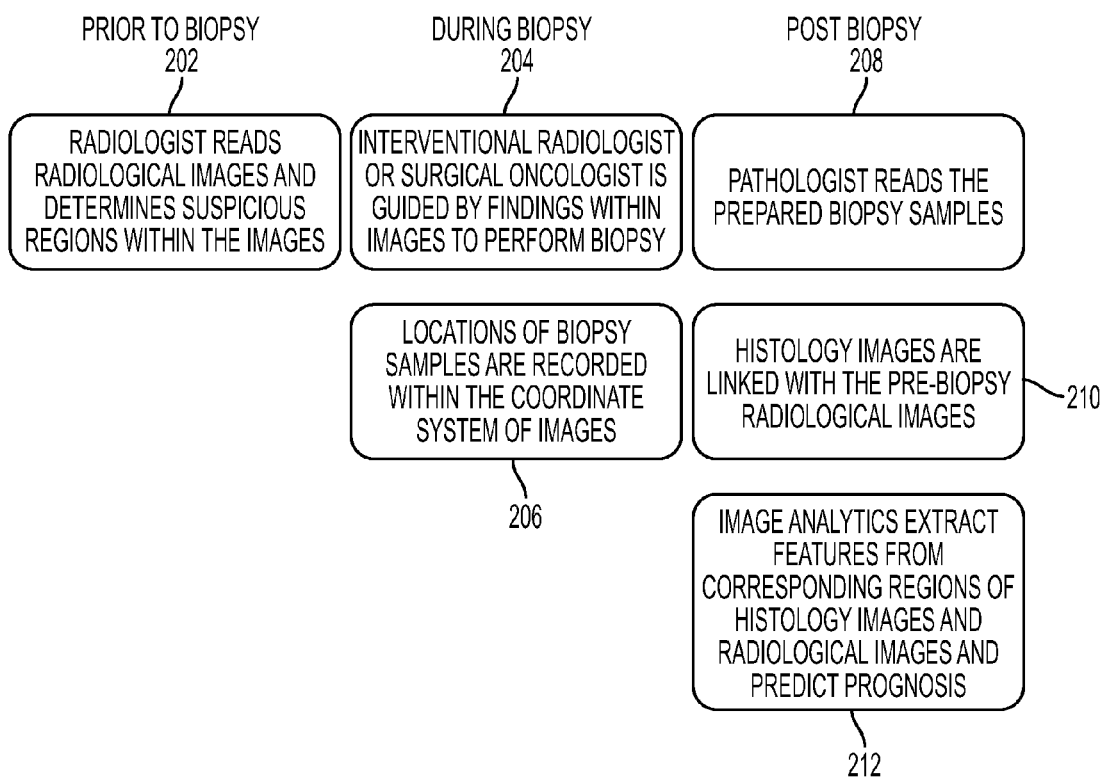
FIG. 2 illustrates a clinical workflow supported by the integrated software platform 102 according to an embodiment of the present invention.

FIG. 2 illustrates a clinical workflow supported by the integrated software platform 102 according to an embodiment of the present invention. As illustrated in FIG. 2, at step 202, prior to a biopsy, a radiologist reads radiological images (e.g., MR, CT, PET, and/or ultrasound images) of a patient and determines suspicious regions within the images. The radiological images can be displayed to the radiologist on the graphical user interface of the software platform. Steps 204 and 206 occur during a biopsy. At step 204, an interventional radiologist or a surgical oncologist or a urologist is guided by the findings within the radiological images to perform the biopsy. At step 206, locations of biopsy samples are recorded within the coordinate system of the radiological images. For example, the locations of the biopsy samples can be recorded within the coordinate system of the radiological images using the method described in United States Published Patent Application No. 2010/0286517, entitled "System and Method for Image Guided Prostate Cancer Needle Biopsy," the disclosure of which is incorporated herein by reference. Steps 208-212 occur after the biopsy. At step 208, a pathologist reads the prepared biopsy samples (e.g., histological slices) resulting from the biopsy. At step 210, the histology images are linked with the pre-biopsy radiological images. In particular, since the location of each biopsy sample was recorded within the coordinate system of the radiological images, each biopsy sample can be associated with pixels in the pre-biopsy radiological images. At step 212, image analytics extract features from corresponding regions of the histology images and the radiological images and predict prognosis. For example, a trained regression function can be used to predict a prognosis based on the features extracted from the histology images and the radiological images. The trained regression function is trained based on feature sets extracted from histology images and radiological images of previous patients and known outcomes for the previous patients. For each patient, outcomes, including a prognosis, therapy or treatment selected, and outcomes of the therapy or treatment, are collected and stored. Once a large cohort of patients with all of the pathological and radiological information and the outcomes are gathered, the software platform 102 is able to detect and summarize the most discriminate features that can be used to differentiate between different outcome classes (e.g., cancer prognosis versus non-cancer prognosis or successful treatment versus non-successful treatment, etc.). This is done by establishing a relationship (through regression) between the feature sets and the different outcomes. Different regression functions can be trained to predict risk scores for various treatment options, as well as to predict a general prognosis of each patient.

Figure 3:
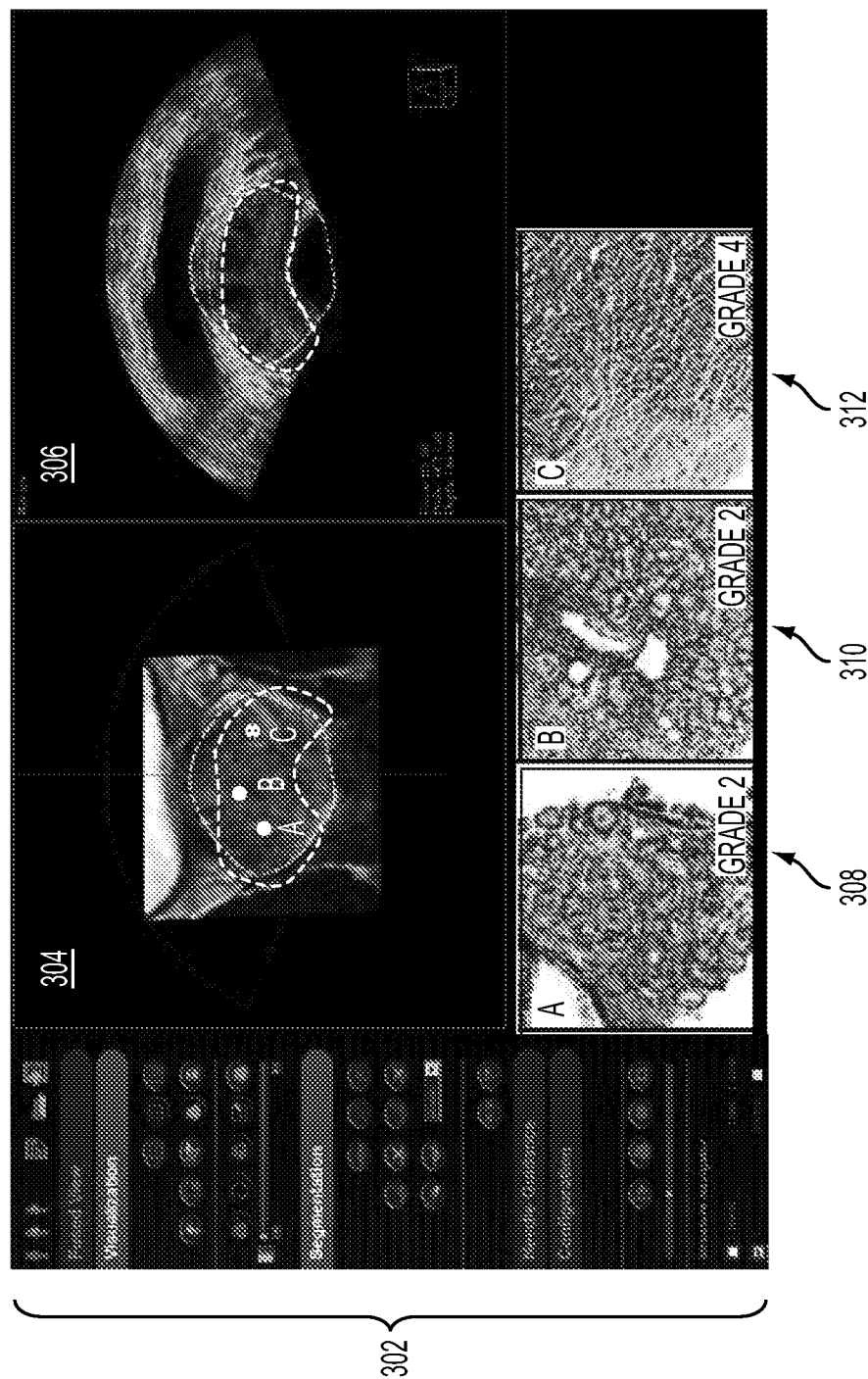
FIG. 3 illustrates an exemplary screenshot of a graphical user interface of the integrate software platform, according to an embodiment of the present invention.

FIG. 3 illustrates an exemplary screenshot of a graphical user interface 300 of the integrate software platform, according to an embodiment of the present invention. As illustrated in FIG. 3, the graphical user interface 300 includes user controls 302 that allow a user to control the software platform and interact with the images displayed in the graphical user interface 300. The graphical user interface 300 displays radiological images 304 and 306. As shown in FIG. 3, image 306 is a transrectal ultrasound image and image 304 is an MR image. Three locations A, B, and C, of biopsy cores are marked on the MR image 304. The corresponding hematoxylin and eosin (H&E) stained histological slices 308, 310, and 312 are also displayed in the graphical user interface 300. Histological slice 308 corresponds to location A in the MR image 304, histological slice 310 corresponds to location B in the MR image 304, and histological slice 312 corresponds to location C in the MR image 304. The analytics can be used to automatically assign a grade to the H&E stained histological slices 308, 310, and 312. As shown in FIG. 3, Gleason grading is automatically performed on the histological slices 308, 310, and 312, resulting in grade 2 being determined for slices 308 and 310 and grade 4 being determined for slice 312. Furthermore, analytics can be applied to the radiological images 304 and 306 and histological slices 308, 310, and 312 to detect other information, such as hyper-vascularity, micro-calcifications, etc., depending on the anatomy and the type of cancer.

Figure 4:
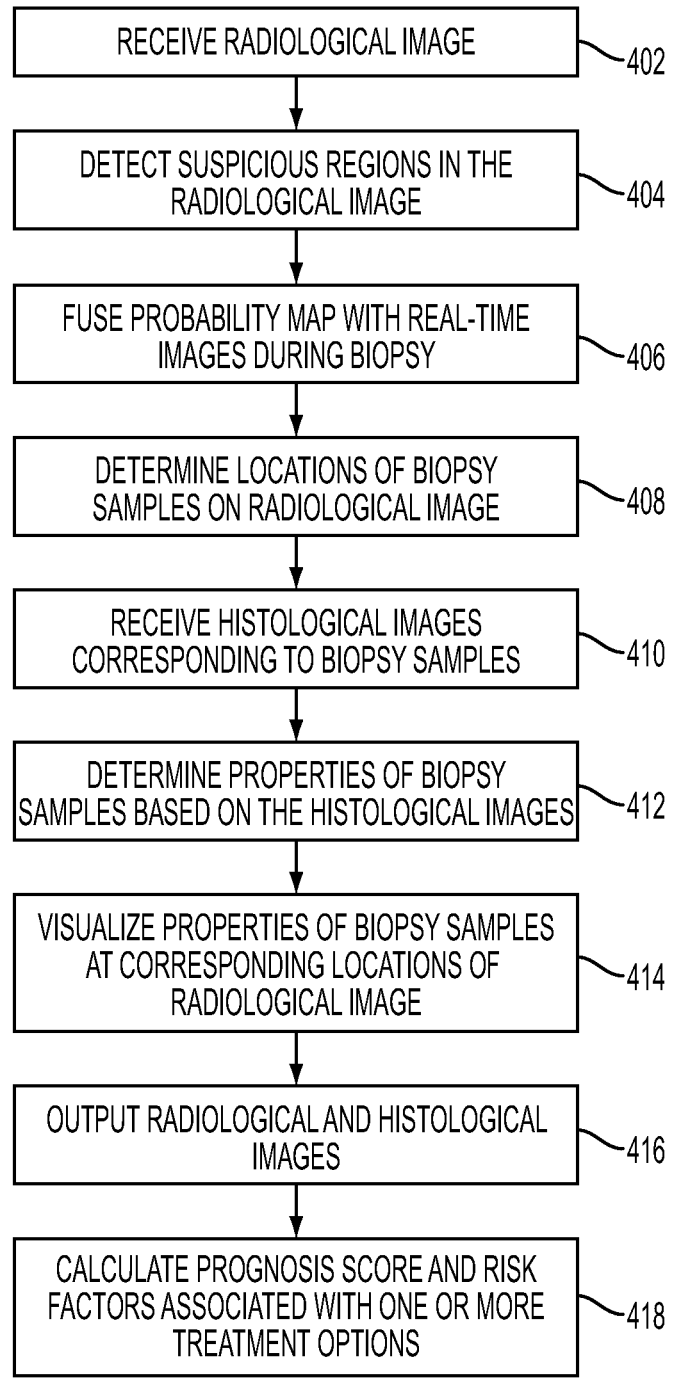
FIG. 4 illustrates a method of integrating radiological and pathological information according to an embodiment of the present invention.

FIG. 4 illustrates a method of integrating radiological and pathological information according to an embodiment of the present invention. As illustrated in FIG. 4, at step 402, a radiological image is received. The radiological image is obtained in a pre-biopsy 2D or 3D imaging scan and includes the region (e.g., prostate, breast, etc.) that will be biopsied. In one embodiment, the radiological image is a MR image, but the present invention is not limited thereto. The radiological image may be generated using any imaging modality, such as CT, MR, ultrasound, molecular imaging (PET/SPECT), etc., or any combination of such modalities. The radiological image may be received directly from an image acquisition device, such as an MR or CT scanner, or may be received by loading a previously stored radiological image.

At step 404, suspicious regions are detected in the radiological image. The suspicious regions can be detected using a trained classifier, such a probabilistic boosting tree (PBT) classifier. The trained classifier is trained based on training data to determine which features in the radiological image are most discriminant is detecting regions in radiological images having a high probability of being cancerous. Previous data processed by the integrated software platform is stored and can then be used to train the classifier. According to an advantageous embodiment, both anatomical regions in the radiological images and the corresponding pathological findings giving detailed cellular level information regarding the tumor can be used as training data to train the classifier. The classifier is used to scan the radiological image and extract features from the radiological image at each pixel and determine for each pixel a probability that the pixel is in a suspicious (cancerous) region. This results in a probability map, in which the each pixel of the radiological image is assigned an intensity based on the probability calculated for that pixel.

At step 406, the probability map generated from the radiological image is fused onto real-time images used to guide a biopsy procedure. Real-time images, such as ultrasound images, can be used to guide the placement of a needle to extract biopsy tissue samples. By registering the probability map onto the real-time images used to guide the biopsy, the points having the highest probability of being in suspicious regions can be seen in the real-time images. This allows the needle to be guided to high probability points in the real-time images to extract the biopsy samples at the high probability points. In an advantageous implementation, the probability map generated from the radiological image is fused to the real-time images using the method described in United States Published Patent Application No. 2010/0286517, entitled "System and Method for Image Guided Prostate Cancer Needle Biopsy," the disclosure of which is incorporated herein by reference.

At step 408, locations of the biopsy samples on the radiological image are determined. In particular, a registration is calculated to fuse the probability map generated from the radiological image to the real-time images used to guide the biopsy. The location of each of each biopsy sample can be mapped from the real-time images to the coordinate system of the original radiological image based on this registration. For each biopsy sample taken during the biopsy, a corresponding location of the biopsy sample (i.e., the position of the needle in the real-time guidance images) is mapped to the radiological image. The corresponding location in the radiological image for each biopsy sample is then stored, for example in a database, on a memory or storage device. Although steps 404-408 illustrate image-based tracking of the biopsy needle to determine the corresponding locations of biopsy locations in the radiological image, the present invention is not limited thereto. In an alternate embodiment, a magnetically tracked biopsy needle can be used to track the position of the biopsy needle and map the locations of the biopsy samples to the radiological image.

At step 410, histological images corresponding to the biopsy samples are received. For example, the histological images may be images of H&E stained slices of the tissue extracted in the biopsy samples. The histological images are stored in the database and loaded into the integrated software platform.

At step 412, properties of the biopsy samples are determined based on the corresponding histological images. In an advantageous embodiment, a cancer grade or score is a property determined for each biopsy sample. The cancer grade for a biopsy sample can be determined automatically or manually based on the corresponding histological image. For manual cancer grade determination, a histological image is displayed and a pathologist visually determines a cancer grade based on the displayed histological image. The cancer grade can be automatically determined using a variety of algorithms. In embodiment, Gleason grades for prostate biopsy samples can be automatically determine from the histological images using the method described in P. Khurd, et al., "Network cycle features: Application to Computer-Aided Gleason Grading of Prostate Cancer Histopathological Images," In *Biomedical Imaging: From Nano to Macro,* 2011 IEEE International Symposium on Biomedical Imaging, pages 1632-1636, the disclosure of which is incorporated herein by reference. Similarly automated algorithms for other cancer grading systems, such as the Nottingham-Bloom-Richardson grading system for breast cancer, may be used to automatically calculate cancer grades for other forms of cancer.

According to an advantageous embodiment of the present invention, another property determined for each biopsy sample can be a localized quantitative measure (or grade) that is calculated based on a combination of features extracted from the histological image and features extracted from the radiological image at the corresponding location. For example, machine-learning techniques can be used to select discriminant features from the features extracted from the histological image and the features extracted from the radiological image based on training data including correlated histological and radiological images. The features of the histological image can include cellular based morphological features, such as those described in P. Khurd, et al., "Network cycle features: Application to Computer-Aided Gleason Grading of Prostate Cancer Histopathological Images," In *Biomedical Imaging: From Nano to Macro,* 2011 IEEE International Symposium on Biomedical Imaging, pages 1632-1636, and the features of the radiological image can include physiological features, such as intensity and gradient based features, vascularity (for example based on perfusion imaging), and micro-calcifications (as appear in both MR and CT images). In one possible implementation, a support vector machine is trained based on such features and used to determine a cancer grade of each biopsy sample based on features extracted from the corresponding histological image and features extracted at the corresponding location of the radiological image. This cancer grade can be determined for each biopsy sample in place of or in addition to the cancer grade determined solely based on the histological image.

At step 414, the properties of the biopsy samples are visualized at the corresponding locations of the radiological image. In one embodiment, an indication the cancer grade for each biopsy sample can be visualized at the corresponding location in the radiological image. For example, the visualizations can be color-coded indicators having different colors corresponding to different cancer grades. In the example of FIG. 3, different color dots can be used at locations A, B, and C in the MR image 304 to visualize the cancer grades of the biopsy samples corresponding to histological images 308, 310, and 312, respectively. For example, the dots at locations A and B in the MR image 304 can be green to indicate that the biopsy samples corresponding to histological images 308 and 310 have a cancer grade of "grade 2", and the dot at location C in the MR image 304 can be red to indicate that the biopsy sample corresponding to the histological image 312 has a cancer grade of "grade 4". Such visualizations can be used to visualize cancer grades determined solely from the histological images and/or cancer grades determined from a combination of the histological images and the radiological image.

In another embodiment, the localized and graded biopsy samples can be used to estimate the focal regions of the cancer via interpolation. For example, the target organ (e.g., prostate) may be segmented (interactively or automatically) in the radiological image and the cancer grading can be interpolated from the biopsy locations in the radiological image to all of the voxels of the target organ in the radiological image. For example, nearest-neighbor interpolation can be used to interpolate the cancer grades from the locations corresponding to the biopsy samples to the rest of the voxels of the target organ.

At step 416, the radiological and histological images are output. In particular, the radiological and histological images, and the properties determined for the biopsy samples are stored to a storage device, and the radiological and histological images are displayed in a graphical user interface. The radiological and histological images are displayed together, such that a location of each histological image is indicated in the radiological image. Furthermore, a visualization indicating the cancer grade and/or visualizations indicating any other localized quantitative measure based on a correlation of both radiological and pathological information are displayed on the radiological image.

At step 418, a prognosis score and risk factors associated with one or more treatment options are calculated by integrating the radiological information from the radiology image and the pathological information from the histological images through regression. In particular, features can be extracted from the histological images and the corresponding locations of the radiological images for all of the biopsy samples. A regression function is trained based on features extracted from histological images and radiological images of previous patients with known outcomes. The regression function establishes a relationship between the feature sets for the patients and the different outcomes. It can be noted, that instead of evaluating correlations between the pathological information and the radiological information locally, at each biopsy sample location, the regression function evaluates the correlation between the radiological information and pathological information globally for a patient to predict a prognosis or select a treatment option for that patient. A different regression function can be used for predicting the prognosis, and for evaluating each of a variety of treatment options (e.g., surgery, ablation, radiation therapy). The regression function that predicts the prognosis can calculate a prognosis score for a patient based on the features exacted from the radiological and histological images for the patient. The regression for each treatment option can calculate a risk factor score for that treatment option based on the features exacted from the radiological and histological images for the patient, and a treatment option can be automatically recommended by selecting the treatment option having the lowest risk factor score.

The features that are extracted from the histological images can include cellular based morphological features, such as those described in P. Khurd, et al., "Network cycle features: Application to Computer-Aided Gleason Grading of Prostate Cancer Histopathological Images," In *Biomedical Imaging: From Nano to Macro*, 2011 IEEE International Symposium on Biomedical Imaging, pages 1632-1636, and the features extracted from the radiological image can include physiological features, such as intensity and gradient based features, vascularity, and micro-calcifications. It is also possible to include as features for the regression function, other biomarkers, including in-vitro diagnostics (both molecular and immunoassay based) performed on either tissue or blood samples. These biomarkers can be integrated with the other features and collectively correlated with a number of outcomes for various treatment procedures.

Figure 5:
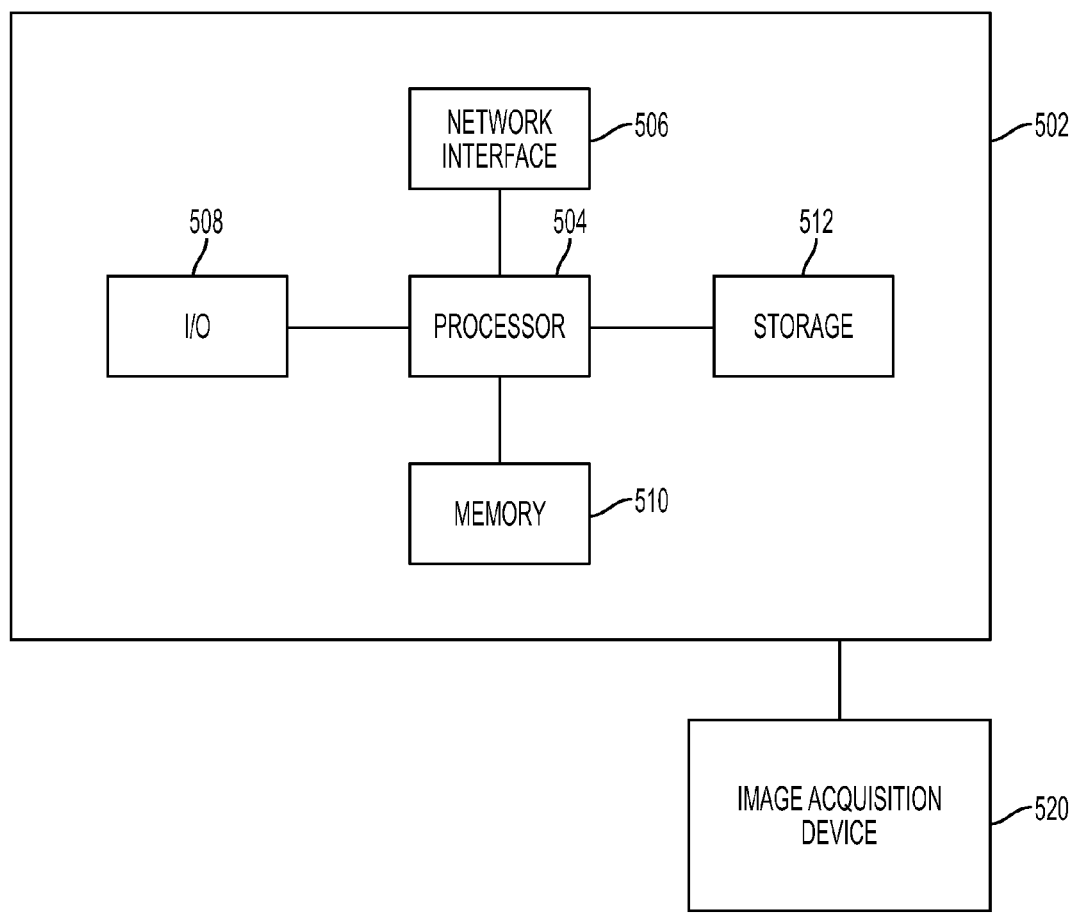
FIG. 5 is a high level block diagram of a computer capable of implementing the present invention.

The above-described methods for integrating pathological and radiological information may be implemented on a computer using well-known computer processors, memory units, storage devices, computer software, and other components. A high level block diagram of such a computer is illustrated in FIG. 5. Computer 502 contains a processor 504 which controls the overall operation of the computer 502 by executing computer program instructions which define such operation. The computer program instructions may be stored in a storage device 512, or other computer readable medium (e.g., magnetic disk, CD ROM, etc.) and loaded into memory 510 when execution of the computer program instructions is desired. Thus, the steps of the method of FIG. 4 may be defined by the computer program instructions stored in the memory 510 and/or storage 512 and controlled by the processor 504 executing the computer program instructions. An image acquisition device 520, such as an MR scanner, CT scanner, PET scanner, ultrasound device, etc., can be connected to the computer 502 to input images to the computer 502. It is possible to implement the image acquisition device 520 and the computer 502 as one device. It is also possible that the image acquisition device 520 and the computer 502 communicate wirelessly through a network. The computer 502 also includes one or more network interfaces 506 for communicating with other devices via a network. The computer 502 also includes other input/output devices 508 that enable user interaction with the computer 502 (e.g., display, keyboard, mouse, speakers, buttons, etc.). One skilled in the art will recognize that an implementation of an actual computer could contain other components as well, and that FIG. 5 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method of integrating radiological and pathological information in cancer diagnosis and treatment, comprising:
   receiving at least one radiological image of a patient;
   determining a location corresponding to each of one or more biopsy samples in the at least one radiological image;
   displaying an integrated display of image information including one or more histological images corresponding to the one or more biopsy samples, the at least one radiological image, and the location corresponding to each of the one or more biopsy samples in the at least one radiological image; and
   automatically predicting a prognosis for the patient based on features extracted from each of the one or more histological images and features extracted from the location corresponding to each of the one or more biopsy samples in the at least one radiological image using a trained regression function.

2. The method of claim 1, wherein the step of determining a location corresponding to each of one or more biopsy samples in the at least one radiological image comprises:
   computing a probability map of suspicious regions in the at least one radiological image;
   registering the probability map to real-time images used to guide a biopsy procedure;
   detecting a needle location and orientation in the real-time images for each of the one or more biopsy samples during the biopsy procedure; and
   mapping the needle location and orientation for each of the one or more biopsy samples from the real-time images to a coordinate system of the at least one radiological image.

3. The method of claim 2, wherein the registering the probability map to real-time images used to guide a biopsy procedure generates a fused visualization of the real-time images and the probability map that highlights regions of high probability within the anatomical context of the real-time images in order to guide the biopsy procedure.

4. The method of claim 3, wherein the step of determining a location corresponding to each of one or more biopsy samples in the at least one radiological image further comprises:
   visualizing the needle using computer graphics on the display during the biopsy procedure to compensate for cases in which the images of the needle are degraded by imaging modality specific artifacts.

5. The method of claim 2, wherein the step of computing a probability map of suspicious regions in the at least one radiological image comprises:
   for each pixel or voxel in the at least one radiological image, computing a probability that the pixel or voxel is in a suspicious region using a trained classifier.

6. The method of claim 2, wherein:
   the step of registering the probability map to real-time images used to guide a biopsy procedure comprises determining a registration to register the probability map to the real-time images; and
   the step of mapping the needle location for each of the one or more biopsy samples from the real-time images to a coordinate system of the at least one radiological image comprises mapping the needle location for each of the one or more biopsy samples from the real-time images to the coordinate system of the at least one radiological image based on the registration determined to register the probability map to the real-time images.

7. The method of claim 2, wherein the at least one radiological image is a magnetic resonance (MR) image and the real-time images used to guide the biopsy procedure are ultrasound images.

8. The method of claim 1, further comprising:
   determining a cancer grade for each of the one or more biopsy samples based on the corresponding one of the one or more histological images; and displaying a visualization indicating the cancer grade for each of the one or more biopsy samples at the corresponding location in the at least one radiological image.

9. The method of claim 8, wherein the step of determining a cancer grade for each of the one or more biopsy samples based on corresponding one of the one or more histological images comprises:
determining a cancer grade for each of the one or more biopsy samples based on features extracted from the corresponding one of the one or more of the histological images and features extracted from the corresponding location in the at least one radiological image.

10. The method of claim 9, wherein the step of determining a cancer grade for each of the one or more biopsy samples based on features extracted from the corresponding one of the one or more of the histological images and features extracted from the corresponding location in the at least one radiological image comprises:
determining the cancer grade for each of the one or more biopsy samples based on the features extracted from the corresponding one of the one or more of the histological images and the features extracted from the corresponding location in the at least one radiological image using a trained support vector machine.

11. The method of claim 8, wherein the step of displaying a visualization indicating the cancer grade for each of the one or more biopsy samples at the corresponding location in the at least one radiological image comprises:
displaying a color-coded indication of the cancer grade for each biopsy sample at the corresponding location in the at least one radiological image.

12. The method of claim 1, further comprising:
automatically predicting a risk factor for one or more treatment options based on features extracted from each of the one or more histological images and features extracted from the location corresponding to each or the one or more biopsy samples in the at least one radiological image using a separate trained regression function for each of the one or more treatment options.

13. The method of claim 12, further comprising:
automatically selecting one of the one or more treatment options based on the risk factor predicted for each of the one or more treatment options.

14. The method of claim 12, wherein the step of automatically predicting a risk factor for one or more treatment options based on features extracted from each of the one or more histological images and features extracted from the location corresponding to each or the one or more biopsy samples in the at least one radiological image using a separate trained regression function for each of the one or more treatment options comprises:
automatically predicting the risk factor for each of the one or more treatment options based on the features extracted from each of the one or more histological images, the features extracted from the location corresponding to each of the one or more biopsy samples in the at least one radiological image, and bio-marker features including in-vitro diagnostics performed on tissue or blood samples, using a separate trained regression function for each of the one or more treatment options.

15. An apparatus for integrating radiological and pathological information in cancer diagnosis and treatment, comprising:
means for receiving at least one radiological image of a patient;
means for receiving one or more histology images of a patient corresponding to one or more biopsy samples;
means for determining a location corresponding to each of the one or more biopsy samples in the at least one radiological image;
means for displaying an integrated display including the one or more histological images corresponding to the one or more biopsy samples, the at least one radiological image, and the location corresponding to each of the one or more biopsy samples in the at least one radiological image; and
means for automatically predicting a prognosis for the patient based on features extracted from each of the one or more histological images and features extracted from the location corresponding to each of the one or more biopsy samples in the at least one radiological image using a trained regression function.

16. The apparatus of claim 15, wherein the means for determining a location corresponding to each of one or more biopsy samples in the at least one radiological image comprises:
means for computing a probability map of suspicious regions in the at least one radiological image;
means for fusing the probability map to real-time images used to guide a biopsy procedure;
means for detecting a needle location in the real-time images for each of the one or more biopsy samples during the biopsy procedure; and
means for mapping the needle location for each of the one or more biopsy samples from the real-time images to a coordinate system of the at least one radiological image.

17. The apparatus of claim 15, further comprising:
means for determining a cancer grade for each of the one or more biopsy samples based on the corresponding one of the one or more histological images; and
means for displaying a visualization indicating the cancer grade for each of the one or more biopsy samples at the corresponding location in the at least one radiological image.

18. The apparatus of claim 17, wherein the means for determining a cancer grade for each of the one or more biopsy samples based on corresponding one of the one or more histological images comprises:
means for determining a cancer grade for each of the one or more biopsy samples based on features extracted from the corresponding one of the one or more of the histological images and features extracted from the corresponding location in the at least one radiological image.

19. The apparatus of claim 15, further comprising:
means for automatically predicting a risk factor for one or more treatment options based on features extracted from each of the one or more histological images and features extracted from the location corresponding to each or the one or more biopsy samples in the at least one radiological image.

20. The apparatus of claim 19, further comprising:
means for automatically selecting one of the one or more treatment options based on the risk factor predicted for each of the one or more treatment options.

21. A non-transitory computer readable medium storing computer program instructions, which when executed on a processor, cause the processor to perform a method comprising:

determining a location corresponding to each of one or more biopsy samples in at least one radiological image of a patient;

displaying an integrated display image and derived information including one or more histological images corresponding to the one or more biopsy samples, the at least one radiological image, and the location corresponding to each of the one or more biopsy samples in the at least one radiological image; and automatically predicting a prognosis for the patient based on features extracted from each of the one or more histological images and features extracted from the location corresponding to each of the one or more biopsy samples in the at least one radiological image using a trained regression function.

22. The non-transitory computer readable medium of claim 21, wherein the step of determining a location corresponding to each of one or more biopsy samples in at least one radiological image comprises:

computing a probability map of suspicious regions in the at least one radiological image;

fusing the probability map to real-time images used to guide a biopsy procedure;

detecting a needle location in the real-time images for each of the one or more biopsy samples during the biopsy procedure; and mapping the needle location for each of the one or more biopsy samples from the real-time images to a coordinate system of the at least one radiological image.

23. The non-transitory computer readable medium of claim 22, wherein:

the step of fusing the probability map to real-time images used to guide a biopsy procedure comprises determining a registration to register the probability map to the real-time images; and the step of mapping the needle location for each of the one or more biopsy samples from the real-time images to a coordinate system of the at least one radiological image comprises mapping the needle location for each of the one or more biopsy samples from the real-time images to the coordinate system of the at least one radiological image based on the registration determined to register the probability map to the real-time images.

24. The non-transitory computer readable medium of claim 21, wherein the method further comprises:

determining a cancer grade for each of the one or more biopsy samples based on the corresponding one of the one or more histological images; and displaying a visualization indicating the cancer grade for each of the one or more biopsy samples at the corresponding location in the at least one radiological image.

25. The non-transitory computer readable medium of claim 24, wherein the step of determining a cancer grade for each of the one or more biopsy samples based on corresponding one of the one or more histological images comprises:

determining a cancer grade for each of the one or more biopsy samples based on features extracted from the corresponding one of the one or more of the histological images and features extracted from the corresponding location in the at least one radiological image.

26. The non-transitory computer readable medium of claim 25, wherein the step of determining a cancer grade for each of the one or more biopsy samples based on features extracted from the corresponding one of the one or more of the histological images and features extracted from the corresponding location in the at least one radiological image comprises:

determining the cancer grade for each of the one or more biopsy samples based on the features extracted from the corresponding one of the one or more of the histological images and the features extracted from the corresponding location in the at least one radiological image using a trained support vector machine.

27. The non-transitory computer readable medium of claim 21, wherein the method further comprises:

automatically predicting a risk factor for one or more treatment options based on features extracted from each of the one or more histological images and features extracted from the location corresponding to each or the one or more biopsy samples in the at least one radiological image using a separate trained regression function for each of the one or more treatment options.

28. The non-transitory computer readable medium of claim 27, wherein the method further comprises:

automatically selecting one of the one or more treatment options based on the risk factor predicted for each of the one or more treatment options.

* * * * *